US00PP20814P2

(12) United States Plant Patent
Bédard

(10) Patent No.: US PP20,814 P2
(45) Date of Patent: Mar. 9, 2010

(54) SHRUB ROSE PLANT NAMED 'DARPELLERIN'

(50) Latin Name: *Rosa hybrida*
Varietal Denomination: Darpellerin

(75) Inventor: Christian Bédard, Brea, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/313,178

(22) Filed: Nov. 18, 2008

(51) Int. Cl.
*A01H 5/00* (2006.01)

(52) U.S. Cl. ..... Plt./107

(58) Field of Classification Search ..... Plt./107
See application file for complete search history.

*Primary Examiner*—Kent L Bell

(57) ABSTRACT

A new variety of Shrub rose suitable for garden decoration, having flowers of pure pink coloration.

1 Drawing Sheet

Classification: The present invention relates to a new *Rosa hybrida* plant.

Variety denomination: The new plant has the varietal denomination 'DARpellerin'.

BACKGROUND OF THE INVENTION

This invention relates to a new and distinct variety of Shrub Rose. It has as its seed parent the variety known as 'AC Marie-Victorin' (U.S. Plant Pat. No. 11,650) and as its pollen parent the variety known as 'Louis Jolliet' (U.S. Plant Pat. No. 9,222).

SUMMARY OF THE INVENTION

Among the features which distinguish the new variety from other presently available and commercial rose cultivars known to the inventor are the following combinations of characteristics: its many stipitate glands on the peduncle, flower receptacle and surface of the bud that bear a strong moss-rose fragrance of sweet juniper, its excellent resistance to powdery mildew, black spot, downy mildew and rust, its high degree of cold hardiness and its strong sweet spicy fragrance. The plant has a bushy very spreading to somewhat climbing growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'DARpellerin' may be asexually propagated by cuttings, budding and grafting. The budding and grafting successfully occurred on the plant/rootstock *Rosa hybrida* cv. 'Dr. Huey' (not patented).

Comparison with Parents

The new rose may be distinguished from its seed parent, 'AC Marie-Victorin' by the following combination of characteristics: whereas 'DARpellerin' bears flowers of pure pink coloration with a strong sweet spicy fragrance, 'AC Marie-Victorin' bears peach-pink flowers with a weak fragrance. The new variety has a bushy very spreading to somewhat climbing medium height to somewhat tall growing habit (about 95 to about 200 cm. in height), whereas the seed parent has a large arching significantly shorter growth habit (about 100 cm. in height).

The new variety may be distinguished from its pollen parent, 'Louis Jolliet' by the following combination of characteristics: whereas 'DARpellerin' bears pure pink flowers of very double petalage (about 33 to 42 petals), 'Louis Jolliet' bears roseine purple flowers with significantly heavier petalage (about 35 to 55 petals). The new variety has a bushy very spreading to somewhat climbing medium height to somewhat tall growing habit (about 95 to about 200 cm. in height), whereas the pollen parent has a spreading and trailing significantly shorter growth habit (about 120 cm. in height).

Comparison with the Closest Commercially Available Cultivar

The closest commercially available cultivar to the new variety is the pollen parent 'Louis Jolliet'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers in clusters of two to six or more per stem. Flowers are borne in regular rounded clusters on strong medium to somewhat long stems (about 26 to about 82 cm.). Outdoors, the plant blooms abundantly and nearly continuously during the growing season. The flowers have a strong sweet spicy fragrance.

BUD

The peduncle is about 2.0 to about 3.5 cm. in length, of average caliper (about 0.2 to about 0.3 cm. in diameter), and usually erect. It is moderately rough, with many stipitate glands, and few hairs. The stipitate glands bear a strong moss-rose fragrance of sweet juniper. Peduncle color is between 146C and 143C.

Before the calyx breaks, the bud is about 1.0 to about 1.5 cm. in diameter at the widest point, about 1.0 to about 1.6 cm. in length, and moderately ovoid to somewhat pointed in shape. The surface of the bud bears few foliaceous appendages and many stipitate glands, usually with slender entire foliaceous parts extending beyond the tip of the bud about ¼ or more of its length. The stipitate glands bear a strong moss-rose fragrance of sweet juniper. Bud color is between 137C and 137D.

The sepals are about 1.6 to about 2.3 cm. in length and about 0.6 to about 0.9 cm. in width at the widest point. The outer surface color of the sepal is between 137C and 137D. The inner surface color of the sepal is near 138B broadly bordered by near 137A. The inner surface of the sepal is covered with fine wooly tomentum; sepal margins are lined with numerous hairs and few stipitate glands.

The receptacle of the flower is of somewhat short to medium length (about 0.4 to about 0.6 cm.) and average to somewhat heavy in caliper (about 0.6 to about 0.9 cm. in diameter). The receptacle is urn-shaped to moderately globular in form. Its surface is moderately rough with many stipitate glands and hairs and with thick fleshy walls. The receptacle color is between 144A and 139B.

As the petals open (after the calyx breaks), the bud is about 1.4 to about 1.9 cm. in diameter at the widest point, about 1.6 to about 2.5 cm. in length, and ovoid to somewhat globular in form. The color of the under surfaces of the newly opened petals is between 60C and 67D. At the point where the petal attaches, there is a moderately small zone of between 2D and 1D. The color of the upper surfaces of the newly opened petals is between 61B and 57A. At the point where the petal attaches, there is a somewhat large zone of between 3D and 2C.

BLOOM

When fully open, the bloom ranges from about 6.0 to about 9.3 cm. in diameter. Petalage is very double with about 33 to 42 petals and about 7 to 9 petaloids irregularly arranged. When partially open, the bloom form is moderately cupped, and the petals are loosely spiraled to cupped with petal edges somewhat reflexed outward. When fully open, the bloom form is moderately cupped to somewhat flat, and the petals are loosely cupped to somewhat flat with petal edges moderately reflexed outward.

PETALS

The substance of the petals is somewhat slight and of moderately thin to medium thickness, with upper surfaces moderately satiny to somewhat shiny and under surfaces shiny. The petals are about 3.5 to about 4.9 cm. in length and about 2.0 to about 4.6 cm. in width at the widest point. Petal margins are entire.

The outer petals are broadly obovate in shape with rounded apices and sometimes notched with one notch.

The inner petals are moderately oblanceolate to somewhat oblong in shape with rounded apices and sometimes notched with one notch.

Petaloids are about 1.1 to about 3.5 cm. in length and about 0.4 to about 2.1 cm. in width at the widest point. Petaloids are irregularly shaped somewhat subulate to oblanceolate with rounded apices.

NEWLY OPENED FLOWER

The under surface color of the outer petals is between 68D and 68C. At the point where the petal attaches, there is a moderately small zone of between 5D and 3D. The upper surface color of the outer petals is between 73B and 68C. At the point where the petal attaches, there is a somewhat large zone of between 5D and 3D.

The under surface color of the intermediate, and inner petals is between 73B and 68C. The upper surface color of the intermediate and inner petals is between 68B and 73B.

The under and upper surface color of the petaloids are similar in coloration to the upper and under surfaces of the intermediate and inner petals.

The general tonality of the newly opened flower is between 68B and 73B.

THREE-DAY-OLD FLOWER

The under surface color of the outer, intermediate and inner petals is between 68D and 68C. At the point where the petal attaches, there is a moderately small zone of between 155B and 155D. The upper surface color of the outer, intermediate and inner petals is between 73C and 68C. At the point where the petal attaches, there is a somewhat large zone of between 155B and 4D.

The under and upper surface color of the petaloids are similar in coloration to the upper and under surfaces of the intermediate and inner petals.

The general tonality of the three-day-old flower is between 73C and 68C.

On the spent bloom, the petals usually drop off cleanly.

In November in Pomona, Calif., blooms on the bush growing outdoors generally last about three to four days. Cut roses from plants grown outdoors and kept at normal indoor living temperatures generally last about three to four days.

MALE REPRODUCTIVE ORGANS

Stamens are many in number (average about 150) and are arranged regularly about the pistils; a few are mixed with petaloids. The filaments are of moderately long length (about 0.6 to about 1.1 cm.) most with anthers. Filaments are between 13C and 14C in color usually heavily suffused with between 53A and 53B. The anthers are somewhat large for the class and all open approximately at the same time. Anther color when immature is near 15C on the external part and near 12D on the internal part. Anther color at maturity is near 165B on the external part and near 200A on the internal part. Pollen is very abundant and between 12D and 13D in color.

FEMALE REPRODUCTIVE ORGANS

Pistils vary in number (average about 65). The styles are even, average in length (about 0.6 to about 0.8 cm.), average in caliper, and columnar to somewhat bunched. Stigma color is between 2C and 3C. Style color is between 150D and 154D. Ovaries are usually all enclosed in the calyx.

Hips have not been observed on this variety when grown in Pomona, Calif.

FOLIAGE

The compound leaves are usually comprised of three to seven leaflets and are borne abundantly. The seven-leaflet leaves are about 6.8 to about 11.9 cm. in length and about 5.6 to about 10.2 cm. in width at the widest point, moderately leathery to somewhat crisp in texture, and semi-glossy to rugose like in finish on the upper side and matte in finish in the under side. The terminal leaflets are about 2.9 to about 5.1 cm. in length and about 1.8 to about 3.1 cm. in width at the widest point, shaped obovate with acute apices and moderately cordate to rounded bases. Their margins are usually simply serrate.

The upper surface color of the mature leaf is between 147A and 141B. The under surface color of the mature leaf is between 138A and 139B. The upper surface color of the young leaf is between 137B and 143A, sometimes lightly suffused toward the edge with between 187B and 183B. The under surface color of the young leaf is between 146B and 143B, sometimes lightly suffused toward the edge with between 187B and 183B.

The rachis is average in caliper and rough. The upper side is shallowly grooved with few hairs and some stipitate glands on the edges of the grooves. The under side of the rachis is rough with some stipitate glands and few small prickles. The rachis color is near 146C on the under side and near 137C on the upper side sometimes lightly suffused on the young leaves with between 187B and 183B.

The stipules are about 1.0 to about 1.5 cm. in length and of moderately wide width (about 0.7 to about 1.0 cm.) with somewhat long straight points that usually turn out at an angle of less than 45 degrees and sometimes recurve toward the stem. The stipule color is near 137A sometimes lightly suffused with between 182A and 183B.

The petiole is average in caliper and rough. The upper side is shallowly grooved with few hairs and some stipitate glands on the edges of the grooves. The under side of the petiole is rough with some stipitate glands and few small prickles. The petiole is about 0.3 to about 0.7 cm. in length and about 0.1 to about 0.15 cm in diameter at the widest point. The petiole color is near 146C on the under side and near 137C on the upper side sometimes lightly suffused on the young leaves with between 187B and 183B.

The plant displays an excellent resistance to powdery mildew, black spot, downy mildew and rust as compared to other commercial varieties grown under comparable conditions in Pomona, Calif. The variety is very winter hardy, surviving winter in USDA zone 3 without any winter protection. The plant's drought and heat tolerance are yet to be determined.

GROWTH

The plant has a bushy very spreading to somewhat climbing medium height to somewhat tail growing habit (about 95 to about 200 cm. in height and about 80 to about 110 cm. spread at the widest point), with moderately full branching. It displays very vigorous growth and the canes are of somewhat light caliper for the class (about 0.8 to about 1.5 cm. in width at the widest point).

The color of the major stems is between 152B and 152C. They bear some large prickles that are about 0.8 to about 1.1 cm. in length. The large prickles are angled moderately to somewhat hooked downward with a moderately short length narrow oval base; prickle color is between 165B and 165C. The major stem bears some small prickles of similar shape and coloration.

The color of the branches is between 146B and 138A. They bear some large prickles which are of similar size and shape to the large prickles on the major stems; prickle color is between 165B and 164B. The branches bear some small prickles of similar shape and coloration.

The color of the new shoots is between 146B and 141C. They bear some large prickles which are of similar size and shape to the large prickles on the major stems; prickle color is between 151A and 145A sometimes lightly suffused with between 187D and 183C. The shoots bear some small prickles of similar shape and coloration.

I claim:

1. A new and distinct Shrub rose plant of the variety substantially as described and illustrated herein.

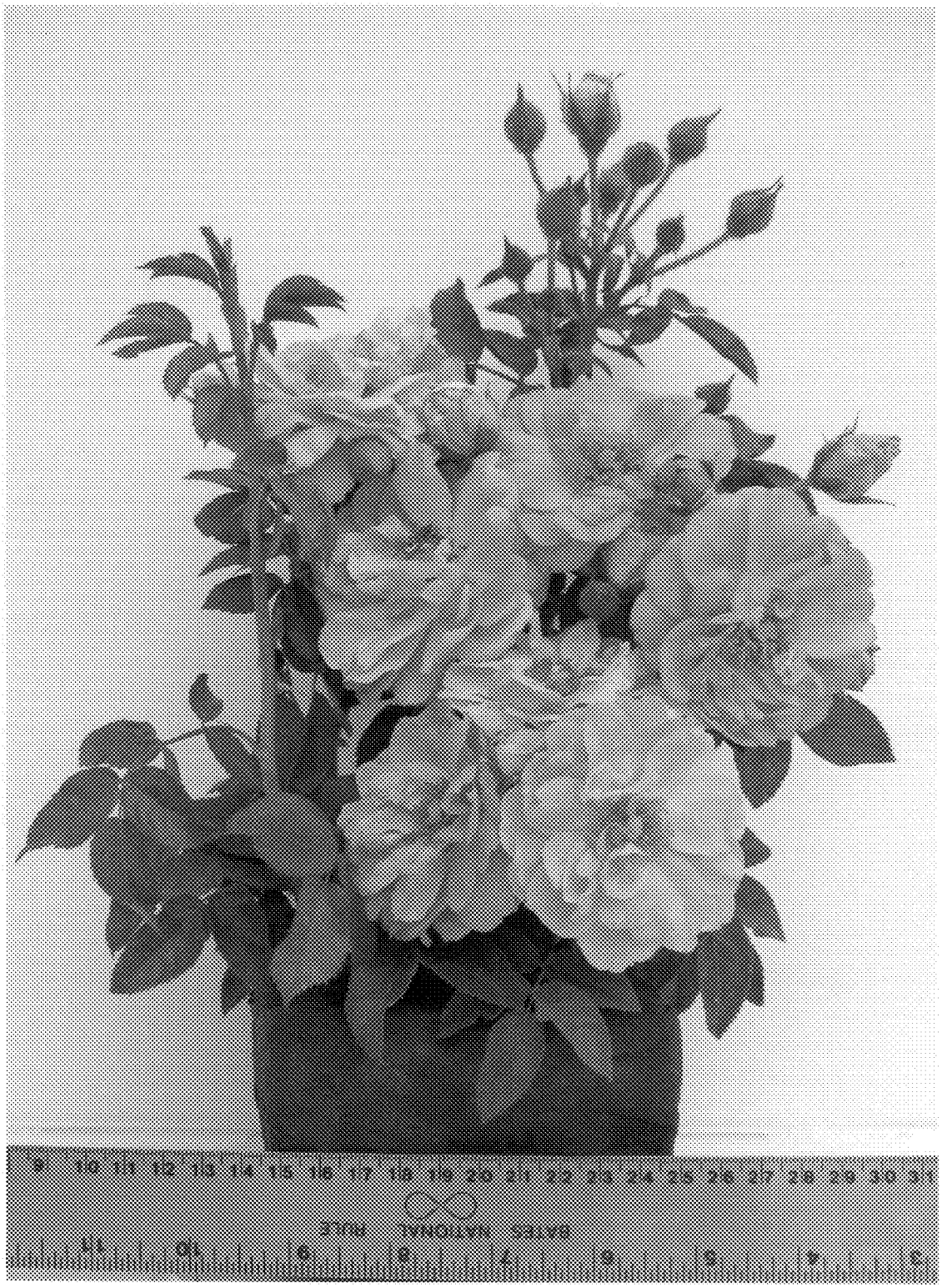

* * * * *